United States Patent [19]

Troutner

[11] Patent Number: 4,501,583
[45] Date of Patent: Feb. 26, 1985

[54] HEMODIALYSIS ACCESS MONITORS

[75] Inventor: Vernon H. Troutner, St. Petersburg, Fla.

[73] Assignee: Extracorporeal, Inc., King of Prussia, Pa.

[21] Appl. No.: 504,659

[22] Filed: Jun. 15, 1983

[51] Int. Cl.³ .......................... A61B 5/02; A61M 5/00; A61M 1/03; G01L 7/08
[52] U.S. Cl. ........................... 604/118; 128/DIG. 13; 200/81.9 R; 210/90
[58] Field of Search .............. 604/118, 121, 122, 123, 604/4, 5, 6; 128/DIG. 12, DIG. 13; 200/81 R, 81.9 R, 83 R, 83 A, 83 B, 83 F, 83 W; 210/90

[56] References Cited

U.S. PATENT DOCUMENTS

| | | | |
|---|---|---|---|
| Re. 29,346 | 8/1977 | Kopp | 604/5 |
| 2,761,445 | 9/1956 | Cherkin | 604/121 |
| 3,731,680 | 5/1973 | Wright et al. | 604/118 X |
| 4,098,274 | 7/1978 | Ebling et al. | 604/118 X |
| 4,194,974 | 3/1980 | Jonsson | 210/90 |
| 4,227,420 | 10/1980 | Lamadrid | 128/675 X |
| 4,231,366 | 11/1980 | Schael | 604/4 |
| 4,309,993 | 1/1982 | Brown | 200/81 R X |
| 4,335,999 | 6/1982 | Lamontagne et al. | 200/81.9 X |
| 4,404,440 | 9/1983 | Busche | 200/83 R |

*Primary Examiner*—William H. Grieb
*Attorney, Agent, or Firm*—Mark A. Hofer

[57] ABSTRACT

A monitoring arrangement is provided for detecting for extreme pressure conditions in blood tubing lines of a hemodialysis system. The arrangement includes a first pushbutton switch and a pivoted lever arm. A clamping means is located at a first end of the lever arm for clamping the blood tubing line against the first pushbutton switch, and the other end of the lever arm opposes a second pushbutton switch. Under low pressure conditions, the blood pressure in the tubing is no longer sufficient to hold the first pushbutton switch closed. The switch then opens to signal a low pressure condition. Under high pressure conditions, the blood tubing pressure causes the lever arm to pivot so that the far end of the lever activates the second pushbutton switch, which signals a high pressure condition.

19 Claims, 4 Drawing Figures

HEMODIALYSIS ACCESS MONITORS

This invention relates to hemodialysis blood flow systems and, in particular, to arrangements for noninvasively monitoring pressure conditions in blood tubing lines.

Hemodialysis blood flow systems are employed as a therapeutic measure when a patient's kidneys no longer perform their blood purifying function by reason of disease, removal or other malfunction. Kidney failure results in the accumulation of toxic wastes in the patient's blood. Unless measures are taken to remove these wastes, the patient will experience potentially fatal uremic poisoning. Uremic poisoning may be prevented through the use of hemodialysis, by which blood is drawn from the patient and circulated through a dialyzer. In the dialyzer, the blood is separated from a specially treated dialysate fluid by a membrane which has pores of microscopic size through which waste products from the blood may pass. The microscopic pores are too small, however, to permit the passage of blood cells, proteins, and other essential elements of the blood through the membrane. The waste products thus diffuse into the dialysate fluid and are removed from the patient's blood. The purified blood is then returned to the patient's body.

Recent advances have led to the development of single needle hemodialysis systems, in which blood is extracted from and returned to the patient's body through a single needle with a Y-shaped junction. The patient is generally prepared for hemodialysis by the surgical implantation of an arteriovenous fistula, which joins an artery with a nearby vein. The diversion of arterial blood into the vein causes the vein to become enlarged, permitting relatively easy insertion of the single needle into the arterialized vein, through which an adequate blood flow for hemodialysis is developed. It has been found that fistula vessels are less traumatized by the single needle technique, and that patients benefit psychologically from the reduced number of venipunctures.

In a typical single needle hemodialysis system, blood is alternately cycled from and to the patient's circulatory system by a single blood pump, or by arterial and venous blood pumps, respectively. During the first, or arterial, phase of operation, blood is drawn from the patient and pumped into the dialysis system by the arterial blood pump. Blood is prevented from returning to the needle by the closure of a valve located between the outlet of the arterial pump and the needle, or through clamping action of the venous blood pump. Blood pressure within the system builds until a time at which the arterial pump is turned off, the valve is opened, or the venous pump in a two-pump system is turned on to pump the blood out of the dialysis system and back to the fistula. During this second, or venous, phase of operation, the pressure of the blood in the dialysis system drops substantially. Eventually a point is reached at which the venous pump is turned off, and the cycle repeats.

It is possible for the needle in the single needle system to become blocked. This could result from the lodging of clotted blood in the needle or, more likely, by the needle becoming dislodged from its normal location in the arterialized vein. The patient may move during the treatment, or an accidental movement may move the blood tubing lines. Such movement could cause the needle to penetrate the wall of the vein, with the needle opening blocked as the needle becomes lodged in muscle tissue.

When the needle is blocked, operation of the arterial blood pump will result in the rapid development of very low blood pressures in the blood tubing line leading to the arterial blood pump. If the venous blood pump is operating when the needle is blocked, excessively high blood pressures will develop in the blood tubing line following the venous blood pump as the pump attempts to force blood into the blocked needle. It is thus desirable to monitor the pressure in the access lines leading to and from the single needle so that the hemodialysis treatment is automatically halted and warnings given if such excessive high or low pressure conditions should develop.

In a single needle hemodialysis system, it is also desirable to minimize the amount of recirculation or mixing of blood between the venous and arterial blood lines. Blood mixing occurs when the arterial blood pump draws purified blood from the line between the venous pump and the needle across the needle junction and back into the system for unnecessary repurification. This condition results primarily from compliance in the access lines to the needle. That is, the arterial blood pump can draw purified blood from the venous line to the extent that venous line compliance will permit. Similarly, the venous pump can force purified blood into the line leading to the arterial pump to the extent that arterial line compliance will allow. Thus it is desirable that any access line monitoring technique not add significantly to access line compliance which would promote blood mixing. Use of a blood line chamber, such as a drip chamber, in combination with a pressure monitor would substantially increase access line compliance, for instance.

In accordance with the principles of the present invention, a monitoring arrangement is provided for the needle access lines in a hemodialysis system. A pressure pillow is located in an access line between the needle and a blood pump. The pressure pillow is located in a clamping arrangement which holds the pillow in place and is sensitive to the occurrence of both excessively high and excessively low blood pressure conditions in the pillow. The detection of either of these conditions activates an alarm and automatically interrupts the hemodialysis treatment.

Figure 1:
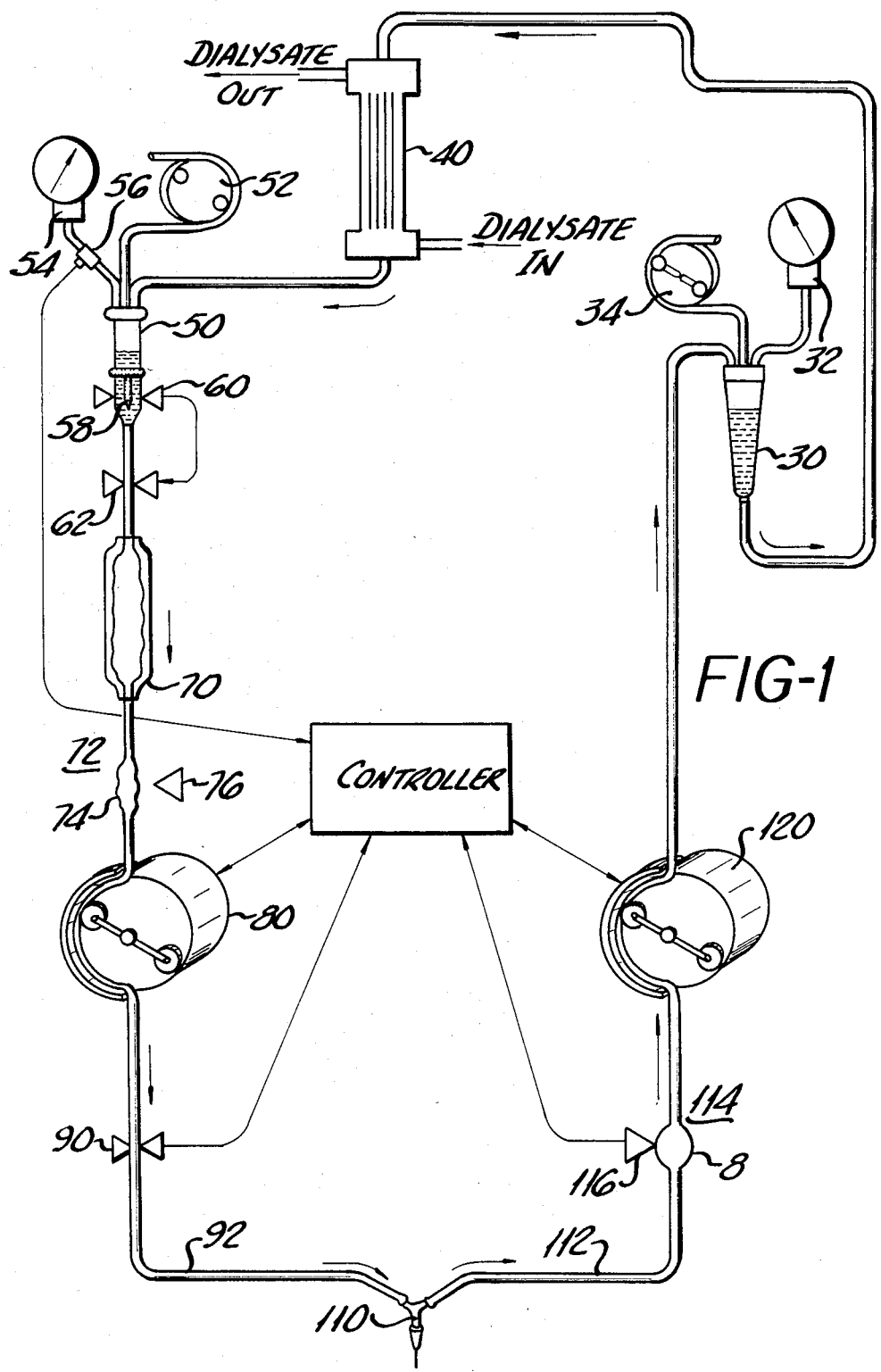
FIG. 1 illustrates the blood circulation path of a single needle hemodialysis system.

Referring to FIG. 1, the blood flow path of a single needle hemodialysis system is shown, including a single needle 110 suitable for the transfer of blood from and to a patient. In FIG. 1, the arrows indicate the direction of the flow of blood through the system.

From the single needle 110, blood flows through the arterial access blood tubing line 112 to an access monitor 114. The access monitor 114 includes a pillow-like section of tubing 8 and a sensor arrangement 116, which will be described subsequently in conjunction with FIGS. 3 and 4. When the pillow pressure declines or increases beyond certain levels the sensor arrangement responds by initiating a system alarm through a controller 100 as well as other procedures which interrupt the operation of the system.

From the access monitor 114 the blood tubing is connected through an arterial roller blood pump 120. The arterial blood pump 120 operates under control of a controller 100. The blood tubing is then connected to a post-pump arterial drip chamber 30 which collects blood and accommodates the connection of various gauges to the system. The pressure in the drip chamber 30 is monitored by an arterial mechanical gauge 32 with alarm contacts. The blood level within the chamber 30 may be varied through the operation of a blood level adjust roller pump 34, by which air may be added to or subtracted from the chamber. The outlet of the drip chamber 30 is connected by blood tubing to the inlet of a capillary dialyzer 40. In the dialyzer, impurities in the blood pass through the dialyzer membrane and into dialysate fluid, which flows into and out of the dialyzer through separate ports under control of a dialysate preparation system (not shown).

Purified blood flows out of the dialyzer 40 and into a venous drip chamber 50. The pressure within the venous drip chamber 50 is monitored by a mechanical venous pressure gauge 54 with alarm contacts. A second blood level adjust pump 52 is connected to the drip chamber 50 to add or subtract air from the chamber, thereby adjusting the blood level within the chamber. In a tubing line between the venous drip chamber 50 and the venous pressure gauge 54 is a solid state pressure transducer 56 which controls the cycling of the blood pumps and also provides another monitor of venous blood pressure. The venous drip chamber 50 further includes a filter 58 located within the chamber.

An air/foam detector 60 is located next to the venous drip chamber 50. The detector 60 ultrasonically or optically detects the presence of an abnormal amount of air or foam in the blood and also monitors the blood level in the chamber 50. The detector responds to the occurrence of such an abnormality by activating a clamp 62, which clamps the blood tubing closed to prevent the pumping of foam and air bubbles into the patient's circulatory system.

The blood tubing is then connected to the inlet of a vinyl accumulator bag 70. The outlet of the accumulator bag 70 is coupled to a positive pressure pillow switch 72, which may be merely an extension of the accumulator bag 70 or, as shown in FIG. 1, may include its own pillow-shaped tubing section 74. Abnormal expansion of the pillow-shaped section 74 in response to an undesirable buildup of blood pressure causes the sensor or switch portion 76 to set off an alarm and to interrupt system operation.

From the pillow switch 72 the blood tubing passes through a venous roller blood pump 80 which is operated under control of the controller 100. The blood tubing then passes through a second air/foam detector 90, which is connected into the system alarm by the controller 100. Finally, the blood tubing is connected to the needle 110 by a venous access blood tubing segment 92 to return the purified blood to the patient's circulatory system. The arrangement of FIG. 1 is described in detail in U.S. Pat. application Ser. No. 423,380, filed Sept. 24, 1982 by the instant inventor and entitled "SINGLE NEEDLE ALTERNATING BLOOD FLOW SYSTEM".

Figure 2:
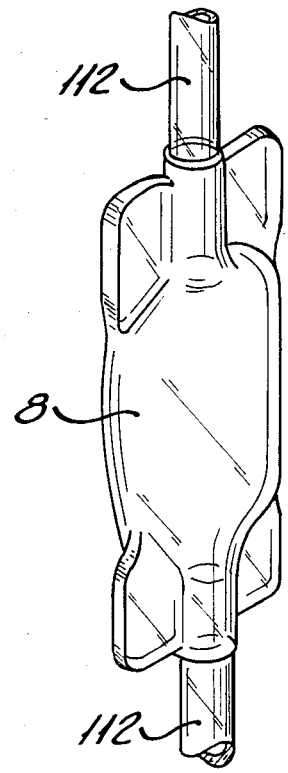
FIG. 2 is a perspective view of a pressure pillow.
Figure 4:
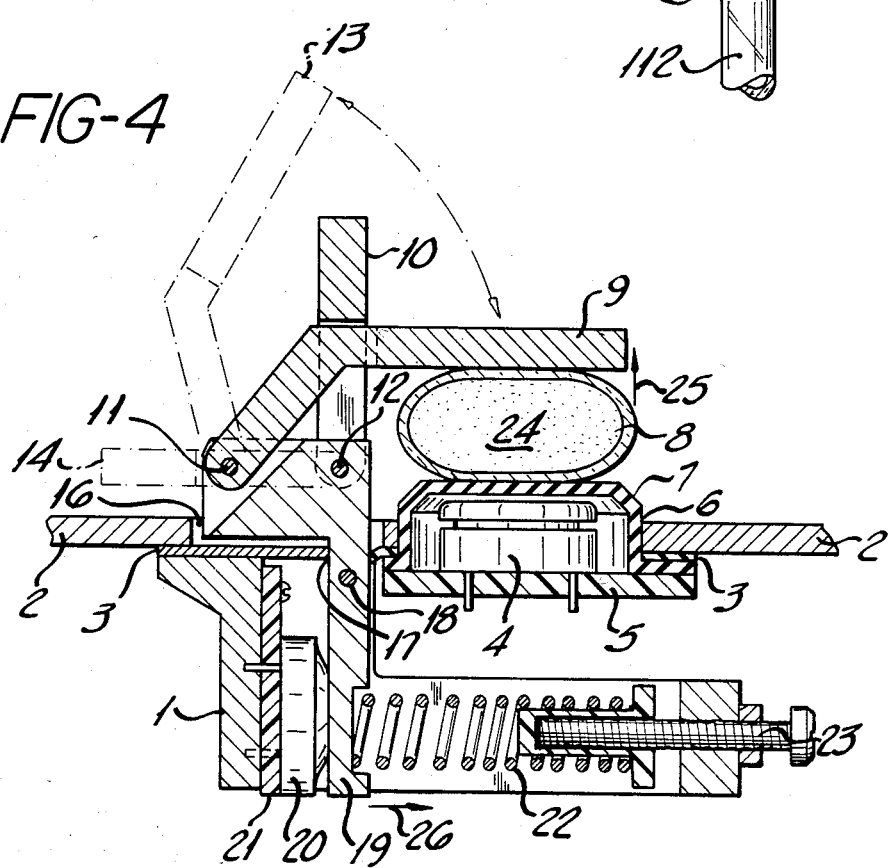
FIG. 4 is a partially cross-sectional top view of the access monitor of FIG. 3.
Figure 3:
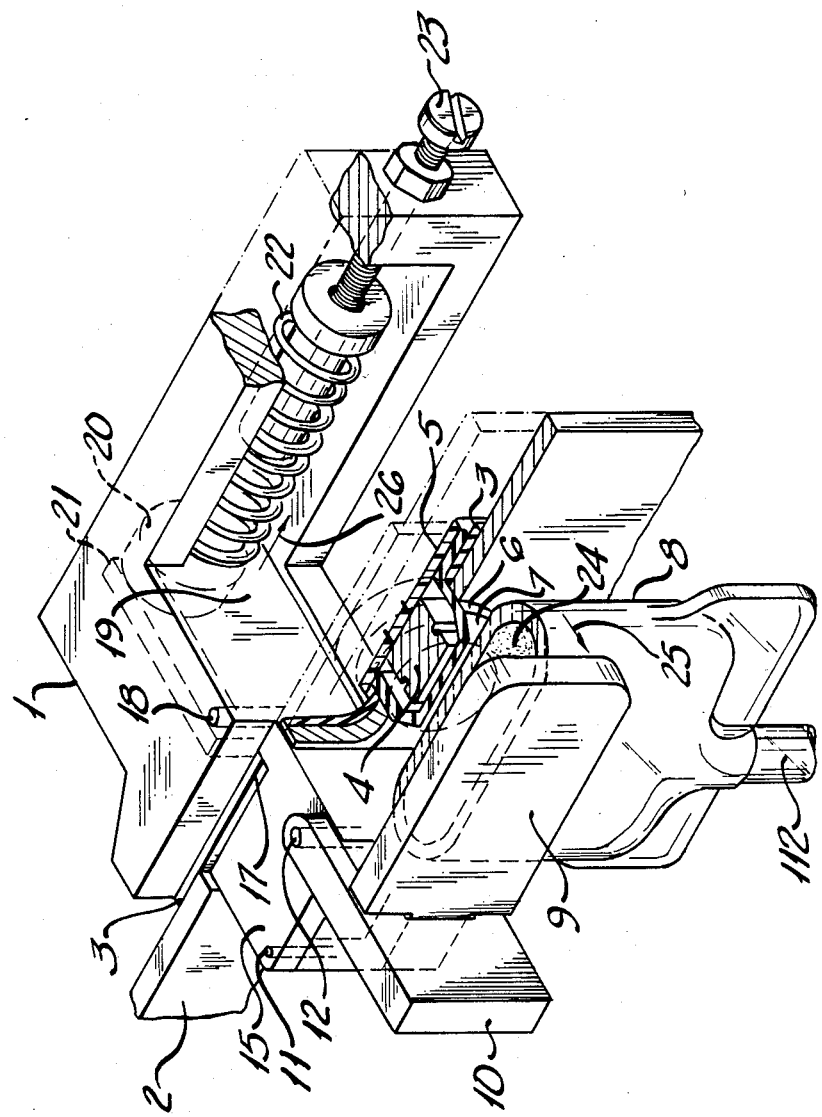
FIG. 3 is a partially cross-sectional perspective view of an access monitor constructed in accordance with the principles of the present invention.

The access monitor 114 is shown in detail in FIGS. 2 through 4. FIG. 2 illustrates the pressure pillow 8 in isolation in the arterial access tubing line 112. The pressure pillow 8 comprises a short section of large tubing thermally formed in an oval shape and connected in the arterial access line 112. The pressure pillow is typically composed of the same Tygon material as the arterial access line.

The pressure pillow 8 is shown located in the sensor arrangement 116 in FIGS. 3 and 4. The access monitor is mounted on a panel of a hemodialysis machine. Portions of the access monitor extend through openings 6 and 16 in the panel 2. A gasket 3 forms an environmental seal around the access monitor at the inside wall of the panel 2. A miniature pushbutton switch 4 is mounted on a circuit board 5 and extends through panel opening 6 inside a protective rubber boot 7. The pressure pillow 8 is positioned over the switch 4.

A clamp 9 holds the pillow 8 against the boot 7 and the switch 4. The clamp is pivoted at a point 11. The clamp 9 is held in its illustrated closed position by a U-shaped bail 10. The ends of the bail 10 are pivoted at a point 12. When the bail 10 is swung ninety degrees to its open position 14 as shown in phantom in FIG. 4, the clamp 9 may then be raised to release the pillow, as indicated by phantom position 13. The clamp and bail thus provide a quick clamp and release mechanism for the pressure pillow.

The clamp 9 and the bail 10 are pivotally connected to a lever 15, which extends through opening 16 in the panel 2 and opening 17 in the gasket 3. The lever 15 is mounted to pivot around a pin 18, which extends through the lever 15 and a base unit 1. The base unit 1 is located in the interior of the machine and is secured to the panel 2. The base unit 1 is used to mount the sensor arrangement 116 with the exception of the pushbutton switch components 4, 5 and 7. The interior end 19 of the lever 15 is located in contact with a second miniature pushbutton switch 20 which is mounted on a second circuit board 21 on the base unit 1. The terminals of the switches 4 and 20 are electrically connected to the controller 100 (not shown).

A compression spring 22 is mounted in the base unit 1 and holds the interior end 19 of the lever 15 against the switch 20. A screw and plug arrangement 23 extends into the end of the spring 22 remote from lever 15 to hold the spring in place and provides a means for adjusting the pressure of the spring against the lever 15.

In operation, blood is located in the interior 24 of the pressure pillow 8, and flows through the pressure pillow when the arterial blood pump is running. Although the pressure pillow is shown located in the arterial access line 112 in FIG. 1, the blood pressure in the pressure pillow is indicative of the pressure in both the arterial and venous access lines 112 and 92 since these two lines are connected through the Y-shaped junction of the needle 110. Thus, the access monitor 114 monitors the pressure in both access lines.

If the needle 110 becomes blocked while the hemodialysis system is in operation, the blocked condition will be detected by the access monitor. Normally, the structural rigidity of the pressure pillow, assisted by the blood pressure in the pillow, holds the pillow between the clamp 9 and the boot 7 and causes switch 4 to close. Should the blockage occur during operation of the arterial blood pump, the blood pressure in the access lines and the pressure pillow will drop below the normal range of arterial phase pressures and below atmospheric pressure. Under these abnormally low pressure conditions, the negative gauge blood pressure in the pillow will allow the surrounding atmospheric pressure to collapse the pillow. Switch 4 will then open, signalling a low pressure condition to the controller 100. The controller will stop blood pump operation and activate audible and visual alarms. The blocked condition must then be remedied before hemodialysis may continue.

If a blocked needle condition should occur during the venous phase of operation, the pumping of blood by the venous blood pump will quickly increase the blood pressure in the access lines and the pressure pillow as the pump attempts to force blood into a blocked needle. The high blood pressure inside the pressure pillow will cause the pillow to press upward against the clamp 9, as indicated by arrow 25 in FIGS. 3 and 4. Movement of the clamp 9 is restrained by the bail 10, and therefore the clamp 9, bail 10 and lever 15 will respond to the pressure by pivoting around the pin 18. The slight pivoting of the lever 16 will cause its interior end 19 to move away from switch 20 as indicated by arrow 26. The switch 20 will then open, thereby signalling a high pressure condition to the controller 100. Again, the controller will respond by stopping the blood pumps and activating audible and visual alarms.

The blood pressure level at which the switch 20 opens in a high pressure condition is determined by adjustment of screw 23 and associated compression spring 22. Typically, the high pressure threshold is set to be above the range of blood pressures encountered during normal operation of the venous blood pump. The blood pressure level at which the switch 4 opens in a low pressure condition is determined by the physical characteristics of the pressure pillow and the spacing between the clamp 9 and the switch 4, as well as the spring pressure of the switch. If desired, a screw can be threaded through clamp 9 with a plate on the end of the screw and in contact with the pressure pillow. The position of the plate could then be adjusted to change the spacing available for the pressure pillow and hence the low pressure switch threshold. It was found acceptable to design the access monitor with a clamp to switch spacing which retained the pillow securely in place. The spacing chosen in a constructed embodiment of the access monitor allowed the switch 4 to open when blood pressure in the pillow dropped below the range of pressures developed during normal operation of the arterial blood pump.

Because a common blood pressure is developed in both the arterial and venous access lines 112 and 92, the access monitor can be located in either the arterial line, as shown in FIG. 1, or in the venous line 92. Locating the access monitor in the arterial line provides an additional benefit, in that blockages due to kinks in the arterial access line may also be detected. Thus, a kink in the arterial access line between the access monitor 114 and the needle 110, which may occur by accidental patient movement, will result in a detected low pressure condition when the arterial blood pump attempts to draw blood through the kinked line. Blockages due to kinks in the venous access line are unlikely to occur because the venous access line is pressurized by the action of the venous blood pump, thereby forcing most accidental kinks out of the line.

The access monitor of the present invention causes no appreciable increase in blood mixing by reason of the negligible contribution to the compliance of the blood tubing by the pressure pillow, and its avoidance of any use of an air chamber device.

What is claimed is:

1. A fluid pressure monitor for detecting the presence of first and second opposite pressure levels relative to an intermediate pressure level in a flexible fluid tubing segment comprising:
   first detection means located on one side of said tubing segment, and responsive to the attainment of said first pressure level in said tubing segment for detecting said first pressure level;
   lever means having a proximal end located on the other side of said tubing segment from said first detection means for retaining said tubing segment between said first detection means and said lever means, a distal end, and a pivot point intermediate said proximal and distal ends for pivoting said lever means in the presence of pressure changes in said tubing segment; and
   second detection means, activated by said distal end of said lever means upon the attainment of said second pressure level in said tubing segment, for detecting said second pressure level.

2. The fluid pressure monitor of claim 1, wherein said detection means include pushbutton switches, and wherein said tubing segment intermediate said lever means and said first detection means include a pressure pillow tubing segment.

3. The fluid pressure monitor of claim 2, wherein said proximal end of said lever means comprises means for clamping said pressure pillow against said pushbutton switch of said first detection means.

4. The fluid pressure monitor of claim 3, wherein said clamping means includes a clamp bar extending over said pressure pillow in its closed position, and a hinged bail for retaining said clamp bar in said closed position.

5. The fluid pressure monitor of claim 4, wherein said distal end of said lever means opposes said second pushbutton switch, and further comprising means for retaining said distal end of said lever means in opposition with said second pushbutton switch.

6. The fluid pressure monitor of claim 5, wherein said retaining means includes a spring which holds said distal end against said second pushbutton switch, and means for adjusting the holding force of said spring.

7. A fluid pressure monitor for detecting the presence of first and second opposite pressure levels relative to an intermediate pressure level in a flexible fluid tubing segment comprising:
   a first switch having a first switch position and a second switch position;
   lever means, having first and second ends and a pivot point intermediate said ends, for urging said fluid tubing segment toward said first switch to cause said first switch to assume its first switch position during said intermediate pressure level condition, and its second switch position during said second pressure level condition; and
   a second switch located in close proximity to said end of said lever mean remote from said tubing segment, said second switch being activated by the pivoting action of said lever means when the pressure in said tubing segment attains said first pressure level.

8. The fluid pressure monitor of claim 7, wherein said fluid tubing segment which is urged toward said first switch includes a pressure pillow tubing segment.

9. The fluid pressure monitor of claim 8, wherein said first end of said lever means comprises means for clamping said pressure pillow toward said first switch, and said second end of said lever means is located in close proximity to said second switch.

10. The fluid pressure monitor of claim 9, wherein said clamping means includes a clamp bar extending over said pressure pillow in its clamping position, and a hinged bail for alternately retaining said clamp bar in its clamping position and for releasing said clamp bar from its clamping position.

11. The fluid pressure monitor of claim 9, wherein said second end of said lever means is retained in close proximity to said second switch by an adjustably tensioned spring.

12. A fluid pressure monitor for detecting the presence of relatively positive and negative pressure levels in a fluid tubing segment comprising:
a base plate;
first switch means mounted on said base plate for detecting said relatively negative pressure level;
lever means having a proximal end for retaining said fluid tubing segment in contact with said first switch means, a distal end, and a pivot point intermediate said proximal and distal ends; and
second switch means located in close proximity to said distal end of said lever means for detecting said relatively positive pressure level when said fluid tubing segment causes said lever means to pivot against said second switch means.

13. The fluid pressure monitor of claim 12, wherein said first switch means comprises a normally open pushbutton switch which opens during said relatively negative pressure level condition.

14. The fluid pressure monitor of claim 13, wherein said proximal end of said lever means retains said fluid tubing segment in contact with said pushbutton switch with a force sufficient to close said pushbutton switch when the pressure level in said tubing segment is greater than said negative pressure level.

15. The fluid pressure monitor of claim 13, wherein said second switch means comprises a normally open pushbutton switch which is closed by said distal end of said lever means when the pressure level in said tubing segment is less than said positive pressure level.

16. The fluid pressure monitor of claim 14, wherein said proximal end of said lever means includes a clamping bar and a bail for alternately retaining said clamping bar in its clamping position and releasing said clamping bar from its clamping position.

17. The fluid pressure monitor of claim 15, further comprising an adjustably tensioned spring for retaining said distal end of said lever means in contact with said pushbutton switch of said second switch means.

18. In a hemodialysis system, apparatus for detecting a predetermined blood pressure level in blood tubing comprising:
a base plate;
a pushbutton switch mounted on said base plate;
a clamp hinge—connected to said base plate at one end and positioned to extend over said pushbutton switch in a closed position for holding said blood tubing against said pushbutton switch; and
a U-shaped bail hinge—connected to said base plate at the ends with said clamp extending through the opening thereof, said bail being moveable to a first position to retain said clamp in said closed position, and to a second position to allow said clamp to be pivotally moved from said closed position.

19. The apparatus of claim 18, further comprising:
a second pushbutton switch; and
means, connected to said clamp, for activating said second pushbutton switch when said clamp is forced away from said first pushbutton switch in said closed position by a given level of force.

* * * * *